(12) United States Patent
Mangel et al.

(10) Patent No.: US 6,429,209 B2
(45) Date of Patent: *Aug. 6, 2002

(54) METHODS FOR TREATING IRRITABLE BOWEL SYNDROME

(75) Inventors: Allen Wayne Mangel, Chapel Hill; Allison Ruth Northcutt, Raleigh, both of NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/834,717

(22) Filed: Apr. 13, 2001

Related U.S. Application Data

(63) Continuation of application No. 09/529,050, filed as application No. PCT/EP98/06278 on Oct. 5, 1998, now Pat. No. 6,284,770.

(30) Foreign Application Priority Data

Oct. 7, 1997 (GB) .............................................. 9721139

(51) Int. Cl.$^7$ ............................................. A61K 31/437
(52) U.S. Cl. .................... 514/292; 514/183; 514/230.5; 514/254.06; 514/284; 514/304; 514/305; 514/306; 514/394; 514/397
(58) Field of Search ............................ 514/183, 254.06, 514/284, 292, 304, 305, 306, 230.5, 394, 397

(56) References Cited

U.S. PATENT DOCUMENTS

| | | | |
|---|---|---|---|
| 5,017,573 A | 5/1991 | Kon et al. ................... | 514/218 |
| 6,284,770 B1 | 9/2001 | Mangel et al. ............... | 514/292 |

FOREIGN PATENT DOCUMENTS

| | | |
|---|---|---|
| EP | 0254584 A | 1/1988 |
| EP | 0279512 A | 8/1988 |
| EP | 0306323 A | 3/1989 |
| EP | 0315390 A | 5/1989 |
| EP | 0336759 A | 10/1989 |
| EP | 0347229 A | 12/1989 |
| EP | 0357416 A | 3/1990 |
| EP | 0364274 A | 4/1990 |
| EP | 0377967 A | 7/1990 |
| EP | 0385722 A | 9/1990 |
| EP | 0387431 A | 9/1990 |
| WO | WO89 09217 A | 10/1989 |
| WO | WO92 05174 A | 4/1992 |
| WO | WO92 10494 A | 6/1992 |
| WO | WO92 11259 A | 7/1992 |
| WO | WO92 12149 A | 7/1992 |
| WO | WO94 01095 A | 1/1994 |

OTHER PUBLICATIONS

K. Bardhan et al., "A Double–Blind, Placebo–Controlled Study to Evaluate the Effocacy of Alosetron in the Treatment of Irritable Bowel Syndrome (IBS)", *Gastroenterology,* vol. 110, No. 4, Apr. 1996, p. A630.

J.M. Foster, et al., "Alosetron Slows Colonic Transit in Patients with Irritable Bowel Syndrome (IBS)", *Gastroenterology,* vol. 112, May 11–14, 1997, p. A732.

D.G. Maxton et al., "Selective 5–hydroxytryptamine antagonism: a role in irritable bowel syndrome and functional dyspepsia?", *Aliment Pharmacol. Ther.,* vol. 10, No. 4, Aug. 1996, pp. 595–599.

J. Zighelboim et al., "Visceral Perception in Irritable Bowel Syndrome", *Dig. Sis. Sci.,*vol. 40, No. 4, Apr. 1995, pp. 819–827.

C.J. Steadman et al., "Selective 5–Hydroxytryptamine Type 3 Receptor Antagonism with OndansetronTreatment for Diarrhea–Predominant Irritable Bowel Syndrome: A Pilot Study", *Mayo Clinic Proc.,* vol. 67, No. 8, Aug. 1992, pp. 732–738.

P.H. Hsyu et al., "Safety and Age, Gender, and Time Dependent Pharmacokinetics of Alosetron", *Pharmaceutical Research,* vol. 12, No. 9 Suppl., Sep. 1995, p. S387.

M. Delvaux et al., "Effect of alosetron on responses to colonic distension in patients with irritable bowel syndrome", *Aliment. Pharmacol, Ther.,* vol. 12, No. 9, Sep. 1998, pp. 849–855.

R. Berkow et al., ED.: "The Merck Manual of Diagnosis and Therapy, 16th edition", 1992, Merck Research Laboratories, Rahway, N.J.,, pp. 841–845.

A. R. Northcutt et al., "Alosetron, A5HT3–Receptor Antagonist, Is Effective in the Treatment of Female Irritable Bowel Syndrome Patients" Gastroenterology, vol. 114, No. 4 part 2, Apr. 1998, p. A812.

*Primary Examiner*—Phyllis G. Spivack
(74) *Attorney, Agent, or Firm*—Lorie Ann Morgan

(57) ABSTRACT

This invention relates to the use of 5-HT3 receptor antagonists in the treatment of nonconstipated female IBS patients.

12 Claims, No Drawings

METHODS FOR TREATING IRRITABLE BOWEL SYNDROME

This application is continuation of U.S. patent application Ser. No. 09/529,050, filed Apr. 5, 2000, U.S. Pat. No. 6,284,770, which is a Rule 371 Application of PCT/EP98/06278, filed Oct. 5, 1998, which claims priority to Great Britain Patent Application No. 9721139.5, filed Oct. 7, 1997.

The invention relates to a new medical use for compounds which act as antagonists of 5-hydroxytryptamine (5-HT) at 5HT$_3$ receptors.

5-HT$_3$ receptor antagonists may be identified by methods well known in the art, for example by their ability to inhibit 3-(5-methyl-1H-imidazoie4-yl)-1-[1-[$^3$H]-methyl-1H-indol-3-yl]-1-propanone binding in rat entorhinal cortex homogenates (following the general procedure described by G Kilpatrick et al, Nature, 1987, 330, 746–748), and/or by their effect on the 5-HT-induced Bezold-Jarisch (B-J) reflex in the cat (following the general method described by A Butler et al, Br. J. Pharmacol., 94, 397–412 (1988)).

A number of different 5-HT$_3$ receptor antagonists have been disclosed, for example those of group A: indisetron, Ro-93777, YM-114, granisetron, talipexole, azasetron, tropisetron, mirtazapine, ramosetron, ondansetron, lerisetron, alosetron, N-3389, zacopride, cilansetron, E-3620, lintopride, KAE-393, itasetron, mosapride and dolasetron.

In UK Patent No. 2209335, incorporated herein by reference, there is disclosed, inter alia, the compound 2,3,4,5-tetrahydro-5-methyl-2-[(5-methyl-1 H-imidazol-4-yl)methyl]-1H-pyrido[4,3-b]indol-1-one, now known as alosetron, which may be represented by the formula (I):

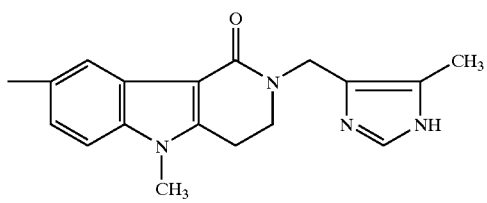

(I)

and pharmaceutically acceptable salts, solvates and pharmaceutically acceptable equivalents thereof, in particular its hydrochloride salt.

5-HT$_3$ receptor antagonists are known to be useful in the treatment of a variety of conditions involving 5-HT$_3$ receptor-mediated mechanisms, including in particular emesis.

Irritable bowel syndrome (IBS) is the most common diagnosis made by gastroenterologists (1) and is characterised by abdominal pain and discomfort and altered bowel functions (2–4). To date, no laboratory or structural defects have been identified in IBS and the formal diagnosis is based upon a constellation of symptoms defined by either the Manning (5) or Rome Criteria (6).

The current understanding of the pathophysiology or aetiology of IBS is limited, and no proven effective therapy is available (3,7). Moreover, many patients gain slight or even no relief from such therapies. Thus, there is a real need to develop new medicines for the treatment of IBS.

Over the last two decades compelling evidence has accumulated that a state of enhanced perception of visceral stimuli develops in patients with IBS (2,3,8–10). In balloon distension studies of the colon or rectum the threshold for sensation of pain is lower in IBS patients compared to controls, and this has been proposed as a biological marker for IBS (11). In view of the evidence for enhanced visceral perception in IBS and the frequent occurrence of pain, any agent considered to be of utility in the treatment of IBS should demonstrate effectiveness in the relief of pain.

Of the classes of therapeutic agents which have been proposed for the treatment of abdominal pain in IBS, 5-HT$_3$ receptor antagonists are among the most promising. In animal models, these agents have been shown to decrease visceral pain responses (12,13). Furthermore, the 5-HT$_3$ receptor antagonist, ondansetron, has been shown to slow colonic transit in normal volunteers (14–15). In patients with IBS ondansetron increases rectal compliance (16) and in diarrhoea-predominant IBS patients ondansetron improves stool consistency (17–19). Ondansetron also inhibits the contractile response of the colon in healthy volunteers in the early postprandial period (20), the time when many IBS patients experience symptoms. A second 5-HT$_3$ receptor antagonist, granisetron, has also been shown to produce a decrease in rectal sensitivity, and reduce post-prandial motor activity in IBS patients (21).

Alosetron is a potent and selective 5-HT$_3$ receptor antagonist, and in preliminary reports, alosetron has been shown to improve abdominal pain (22), and to slow colonic transit in IBS patients (23).

Surprisingly, it has now been found that 5-HT$_3$ receptor antagonists represent a particularly effective and well tolerated therapy in nonconstipated female IBS patients.

According to one aspect the invention therefore provides a 5-HT$_3$ receptor antagonist or a pharmaceutically acceptable derivative thereof for use in the treatment of nonconstipated female IBS.

In one preferred aspect the invention provides a 5-HT$_3$ receptor antagonist or a pharmaceutically acceptable derivative thereof for use in the treatment of diarrhoea predominant female IBS.

In another preferred aspect the invention provides a 5-HT$_3$ receptor antagonist or a pharmaceutically acceptable derivative thereof for use in the treatment of alternating constipation/diarrhoea IBS.

By pharmaceutically acceptable derivative is meant any pharmaceutically acceptable salt or solvate of a 5-HT$_3$ receptor antagonist or any other compound, which upon administration to the recipient is capable of providing (directly or indirectly) a 5-HT$_3$ receptor antagonist or an active metabolite or residue thereof.

In one preferred aspect the invention provides a compound of Group A or a pharmaceutically acceptable derivative thereof for use in the treatment of nonconstipated female IBS.

In a further preferred aspect the invention therefore provides alosetron or a pharmaceutically acceptable derivative thereof for use in the treatment of nonconstipated female IBS.

Suitable pharmaceutically acceptable salts of alosetron include acid addition salts formed with inorganic or organic acids (for example hydrochlorides, hydrobromides, sulphates, phosphates, benzoates, naphthoates, hydroxynaphthoates, p-toluenesulphonates, methanesulphonates, sulphamates, ascorbates, tartrates, salicylates, succinates, lactates, glutarates, glutaconates, acetates, tricarballylates, citrates, fumarates and maleates), and solvates (for example hydrates) thereof.

In a preferred embodiment of the present invention alosetron is employed in the form of its hydrochloride.

In another aspect, the invention provides the use of a 5-HT$_3$ receptor antagonist or a pharmaceutically acceptable derivative thereof in the manufacture of a medicament for the treatment of nonconstipated female IBS.

In another aspect, the invention provides a method of treatment of nonconstipated female IBS which comprises administering an effective amount of a 5-HT$_3$ receptor antagonist or a pharmaceutically acceptable derivative thereof.

Within the above aspects and preferred aspects of the invention, the use of a 5-HT$_3$ receptor antagonist of Group A, more preferably alosetron, is especially preferred.

It is to be understood that reference to treatment includes both treatment of established symptoms and prophylactic treatment, unless explicitly stated otherwise.

Conveniently, a 5-HT$_3$ receptor antagonist or a pharmaceutically acceptable derivative thereof may be formulated in conventional manner using one or more pharmaceutically acceptable carriers or excipients. Thus a 5-HT$_3$ receptor antagonist or a pharmaceutically acceptable derivative thereof may, for example, be formulated for oral, sublingual, buccal, parenteral, rectal or intranasal administration, or in a form suitable for administration by inhalation or insufflation (either through the mouth or nose), or in a form suitable for topical administration.

For oral administration the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium phosphate); lubricants (e.g. magnesium stearate, talc or silica); disintegrates (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl-p-hydroxybenzoates or sorbic acid).

For buccal administration the compositions may take the form of tablets or lozenges formulated in conventional manner.

For parenteral administration the compositions may take the form of injections, conveniently intravenous, intramuscular or subcutaneous injections, for example bolus injections or continuous intravenous infusions. Formulations for injection may be presented in unit dosage form e.g. in ampoules or in multi-dose containers, optionally with an added preservative.

The compositions for parenteral administration may take such forms as suspensions, solutions or emulsions in oily or aqueous vehicles, and may contain formulatory agents such as suspending, stabilising and/or dispersing agents. Alternatively, the compositions may be in dry form such as a powder, crystalline or freeze-dried solid for constitution with a suitable vehicle, e.g. sterile pyrogen-free water or isotonic saline before use. They may be presented, for example, in sterile ampoules or vials.

For rectal administration the compositions may take the form of suppositories or retention enemas.

Tablets for sub-lingual administration may be formulated in a conventional manner.

For intranasal administration, or administration by inhalation or insufflation, conventional formulations may be employed.

For topical administration the pharmaceutical compositions may be liquids, for example solutions, suspensions or emulsions presented in the form of creams or gels.

In addition to the formulations described previously, the compositions may also be formulated as a depot preparations. Such long acting formulations may be administered by implantation (for example subcutaneously, transcutaneously or intramuscularly) or by intramuscular injection. Thus, for example, the compositions may be formulated with suitable polymeric or hydrophobic materials (for example as an emulsion in an acceptable oil) or ion exchange resins, or as sparingly soluble derivatives, for example, as a sparingly soluble salt.

It will be appreciated that the precise therapeutic dose of a 5-HT$_3$ receptor antagonist, expressed in the form of its free base, will depend on the age and condition of the patient and the nature of the IBS to be treated, and will be at the ultimate discretion of the attendant physician.

However, in general, effective doses for the treatment of nonconstipated female IBS patients will lie in the range of 0.001 to 500 mg, such as 0.01 to 100 mg, preferably 0.05 to 50 mg, for example 0.5 to 25 mg per unit dose, which could be administered in single or divided doses, for example, 1 to 4 times per day.

In a preferred embodiment, effective doses of alosetron for the treatment of nonconstipated female IBS patients will lie in the range of 0.01 to 100 mg, such as 0.05 to 50 mg, preferably 0.1 to 25 mg, for example 0.5, 1, 2 or 4 mg of alosetron per unit dose, which could be administered in single or divided doses, for example, 1 to 4 times per day.

The use of alosetron in the treatment of nonconstipated female IBS patients is supported by the following clinical data.

Patients

Three hundred and seventy IBS patients were randomised for study: 80 were randomised to treatment with placebo BID, 72 to 1 mg BID alosetron, 74 to 2 mg BID alosetron, 76 to 4 mg BID alosetron and 68 to 8 mg BID alosetron. Table 1 shows the demographic characteristics for patients in all 5 treatment groups, and characteristics were similar between treatment arms. Patients were required to have symptoms which fulfilled the Rome Criteria for IBS (5) for at least 6 months. Because of the ability of 5-HT$_3$-receptor antagonists to slow colonic transit (14–15), constipation-predominant IBS patients were excluded from this study, and only patients with diarrhoea-predominant IBS or alternating constipation/diarrhoea were included.

Study Design

Daily and weekly symptom data were collected using a recently described electronic touch-tone telephone based system (24,25). Patients underwent a 2 week screening period with no IBS treatment to ensure sufficient baseline level of abdominal pain as well as compliance with the data collection system. Pain was assessed daily on a 5 point scale (0=none; 1=mild; 2=moderate; 3=intense; 4=severe). Average baseline pain over the 2 week screening period was required to be between 1.5–3.3, inclusive, and at least 4 days with at least moderate pain was required for enrolment into the study. Stool consistency data were also collected (1=very hard; 2=hard; 3=formed; 4=loose; and 5=watery). During the screening period an average stool consistency score of $\geq 2.5$ was required for entry into the study in order to exclude those with predominant constipation.

Following the screening period, eligible patients were randomised with equal allocation to 12 weeks of study medication (BID) of placebo or alosetron 1, 2, 4 or 8 mg taken prior to meals. Patients were followed for 2 weeks post-treatment. During the screening period, treatment phase and follow-up period, patients were asked daily questions about their IBS symptoms. Once every 7 days, during the treatment phase of the study, patients responded to an additional question as to whether they had obtained adequate relief of their IBS-related abdominal pain and discomfort during the previous 7 days.

Statistics

For this study, a responder was prospectively defined as a patient who completed the treatment phase of the study and reported adequate relief of their IBS pain and discomfort for at least 6 weeks. Responders for adequate relief have been shown to display a strong correlation with improvement in abdominal pain, bowel function and quality of life as compared to nonresponders (26). In addition, a monthly responder was defined as a patient who reported adequate relief of their IBS pain and discomfort for at least 2 weeks per month. For the monthly analysis, a last observation carried forward procedure was employed, whereby a month with all missing weeks was assigned the number of weeks with adequate relief from the previous non-missing month. Thus, this analysis satisfied the Intent-to-Treat principle by including all patients and months. Treatment groups were compared for the proportion of patients defined as responders, for both endpoints, using a Mantel-Haenszel test stratified for investigator cluster. Finally, the proportion of weeks with adequate relief was compared between treatment groups using a log-rank test.

Daily stool consistency scores and daily number of bowel movements were averaged over the baseline, weekly for weeks 1–4, and monthly (weeks 1–4, 5–8, and 9–12) intervals. In addition, the proportion of days patients experienced a sense of urgency was calculated over the monthly and weekly intervals. For the monthly intervals, the treatment groups were compared for change from baseline using a van Elteren test adjusted for investigator cluster. For the weekly intervals, the treatment groups were compared at each week using a van Elteren test adjusted for-investigator cluster.

Adequate Relief of Pain and Discomfort

| % Responders | Placebo | Alosetron (mg BID) | | | |
|---|---|---|---|---|---|
| | | 1 | 2 | 4 | 8 |
| FEMALE | 33 | 60 | 59 | 51 | 52 |
| MALE | 53 | 20 | 50 | 54 | 52 |

Examination of each dose of alosetron showed a greater proportion of female responders for adequate relief as compared with placebo. The largest treatment effect occurred with 1 mg BID alosetron where 27% more responders were observed as compared to that seen with placebo (33% placebo vs 60% alosetron; p=0.013). A similar result was observed with 2 mg BID alosetron where 59% responders were seen (p=0.026). No meaningful improvement relative to placebo was seen in the male population with any dose of alosetron. However, the placebo response in males was substantially greater than that seen in females.

| % Weeks with adequate relief | Placebo | Alosetron (mg BID) | | | |
|---|---|---|---|---|---|
| | | 1 | 2 | 4 | 8 |
| FEMALE | 33 | 58 | 50 | 50 | 50 |

The proportion of weeks with adequate relief was also evaluated. Placebo treated female patients had a median 33% of weeks with adequate relief. With 1 mg BID alosetron, female patients reported adequate relief for a median 58% of the weeks (p=0.039). In the treatment groups receiving greater than 1 mg alosetron (i.e., 2 mg, 4 mg and 8 mg BID) female patients reported having adequate relief for a median 50% of the weeks with each of the doses of alosetron. By contrast, male patients received no meaningful benefit with respect to the proportion of weeks with adequate relief with alosetron.

| % Responders | Monthly Intervals | | |
|---|---|---|---|
| | 1 | 2 | 3 |
| Placebo | 32 | 42 | 36 |
| Alosetron 1 mg BID | 53 | 62 | 60 |

In order to identify how rapidly alosetron produces adequate relief, we analysed adequate relief during each of the three months of the study. With 1 mg BID alosetron, statistically significant improvement occurred for female patients during each month. Increases of 21%, 20% and 24% above placebo were seen at months 1,2 and 3, respectively. Alosetron 1 mg was superior to the other alosetron (2,4, or 8 mg) evaluated. No improvement relative to placebo was seen among males at any month, with any dose of alosetron.

Improvement in Bowel Habits

In females patients, most doses of alosetron significantly improved stool consistency, bowel movement frequency and the proportion of days with urgency as compared to placebo (Table 2). For each of these parameters, a statistically significant benefit over placebo was achieved after 1 week of treatment and benefit persisted throughout the remainder of the 12 week treatment period. Among males, no significant improvement over placebo was seen in the bowel-related functions with the exception of stool consistency. Stool consistency in males improved significantly with doses of alosetron higher than 1 mg BID.

These results demonstrate that alosetron significantly improved abdominal pain and bowel function in female IBS patients. Alosetron also significantly improved, in female patients, three clinically relevant bowel related functions: number of bowel movements per day, stool consistency, and sense of urgency. All of these parameters were significantly improved within the first week of treatment and were sustained throughout the three month study.

Surprisingly, alosetron-mediated improvement in the efficacy parameters, with the exception of hardening in stool consistency, were found to occur only in females.

Based upon the results of the present study, alosetron appears to represent an effective and well tolerated therapy in nonconstipated female IBS patients.

TABLE 1

Demographic Characteristics

| Characteristic | Placebo | Alosetron BID | | | |
| --- | --- | --- | --- | --- | --- |
| | | 1 mg | 2 mg | 4 mg | 8 mg |
| n | 80 | 72 | 74 | 76 | 68 |
| Age (yrs) | 43.3 ± 14.9 | 44.7 ± 13.5 | 43.9 ± 14.9 | 44.3 ± 11.9 | 45.1 ± 14.8 |
| Sex | | | | | |
| Male | 21 (26%) | 19 (26%) | 23 (31%) | 21 (28%) | 28 (41%) |
| Female | 59 (74%) | 53 (74%) | 51 (69%) | 55 (72%) | 40 (59%) |
| Race | | | | | |
| Caucasian | 76 (95%) | 67 (93%) | 67 (91%) | 75 (99%) | 63 (93%) |
| Black | 3 (4%) | 3 (4%) | 4 (5%) | 0 (0%) | 0 (0%) |
| Other | 1 (1%) | 2 (3%) | 3 (4%) | 1 (1%) | 5 (6%) |
| Females | | | | | |
| Post-Menopausal | 10 (17%) | 9 (17%) | 9 (18%) | 9 (16%) | 8 (20%) |
| Sterile | 25 (42%) | 29 (55%) | 25 (49%) | 35 (64%) | 19 (48%) |
| Child-bearing Potential | 24 (41%) | 15 (28%) | 17 (33%) | 11 (20%) | 13 (33%) |
| Duration of IBS Symptoms (yrs) | 9.8 ± 10.9 | 10.3 ± 10.4 | 9.4 ± 9.9 | 9.9 ± 9.3 | 9.3 ± 7.7 |
| Baseline Pain | 2.23 ± 0.47 | 2.12 ± 0.48 | 2.11 ± 0.42 | 2.22 ± 0.48 | 2.30 ± 0.47 |

Pain score: 0= none, 1= mild, 2= moderate, 3= intense, 4= severe

TABLE 2

Effects of Alosetron on Bowel Function In Female Patients With IBS

| Function (n) | Placebo (59) | Alosetron BID | | | |
| --- | --- | --- | --- | --- | --- |
| | | 1 mg (53) | 2 mg (51) | 4 mg (55) | 8 mg (40) |
| % Days with Urgency | 54.3 ± 32.04 | 33.0 ± 28.8* | 35.9 ± 34.4** | 37.8 ± 34.2* | 41.5 ± 33.6 |
| Stool # per day | 2.2 ± 1.35 | 1.4 ± 1.0* | 1.7 ± 0.9* | 1.8 ± 1.2* | 1.3 ± 0.7* |
| Stool Consistentcy | 2.9 ± 0.69 | 2.1 ± 0.83 | 2.2 ± 0.73 | 2.4 ± 0.74 | 1.8 ± 0.64 | mean ± SD
Data collected from week 9–12 interval
p-values are based on change from baseline
*p ≦ 0.01 with respect to placebo
**p ≦ 0.001 with respect to placebo
Consistency score: 1= very hard, 2= hard, 3= formed, 4= loose, 5= watery

References

1. Everhart J J, Renault P F. Irritable bowel syndrome in office-based practice in the United States. Gastroenterology 1991; 100:998–1005.
2. Mayer E A, Gebhart G F. Basic and clinical aspects of visceral hyperalgesia. Gastroenterology 1994; 107:271–93.
3. Camilleri M, Choi M-G. Review article: irritable bowel syndrome. Aliment. Pharm. Ther. 1997; 11:3–15.
4. Drossman DA. Chronic functional abdominal pain. Am. J. Gastroent. 1996; 91:2270–81.
5. Manning A P, Thompson W G, Heaton K W, Morris A F. Towards a positive diagnosis of the irritable bowel. Br. Med. J. 1978; 2:653–4.
6. Thompson W G, Dotevall G, Drossman D A, Heaton K W, Kruis W. Irritable bowel syndrome: guidelines for the diagnosis. Gastroent. Int. 1989; 2:92–5.
7. Klein K B. Controlled treatment trials in the irritable bowel syndrome: a critique. Gastroenterology 1988; 95:232–41.
8. Ritchie J. Pain from distension of the pelvic colon by inflating a balloon in the irritable colon syndrome. Gut 1973; 14:125–132.
9. Whitehead W E, Holtkotter B, Enck P, Hoelzl R, Holmes K D, Anthony J, Shabsin H S, Schuster M M. Tolerance for rectosigmoid distension in irritable bowel syndrome. Gastroenterology 1990; 98:1187–92.
10. Bueno L, Fioramonti J, Delvaux M, Frexinos J. Mediators and pharmacology of visceral sensitivity: from basic to clinical investigations. Gastroenterology 1997; 112:1714–43.
11. Mertz H, Naliboff B, Munakata J, Niazi N, Mayer E A. Altered rectal perception is a biological marker of patients with irritable bowel syndrome. Gastroenterology 1995; 109:40–52.
12. Moss H E, Sanger G J. The effects of granisetron, ICS 205–930 and ondansetron on the visceral pain reflex induced by duodenal distension. Br. J. Pharm. 1990; 100:497–501.
13. Scott C M, Grundy D, Boissonade F, Bountra C. Alosetron inhibits the colorectal distension-evoked depressor response and spinal c-fos expression in the anesthetized rat. Gastroenterology 1997; 112:A822.
14. Gore S, Gilmore I T, Haigh C G, Brownless S M, Stockdale H, Morris A I. Colonic transit in man is slowed by ondansetron (GR38032F), a selective 5-hydroxytryptamine receptor (type 3) antagonist. Aliment. Pharm. Ther. 1990; 4:13944.
15. Talley N J, Phillips S F, Haddad A, Miller L J, Twomet C, Zinsmeister A R, MacCarty R L, Ciociola A. GR 38032F (ondansetron), a selective 5-$HT_3$ receptor antagonist, slows colonic transit in healthy man. Dig. Dis. Sci. 1990; 35:477–80.
16. Zighelboim J, Talley N J, Phillips S F, Harmsen W S, Zinsmeister A R. Visceral perception in irritable bowel syndrome. Rectal and gastric responses to distension and serotonin type 3 antagonism. Dig. Dis. Sci. 1995; 40:819–27.
17. Steadman C J, Talley N J, Phillips S F, Zinsmeister A R. Selective 5-hydroxytryptamine receptor antagonism with ondansetron as treatment for diarrhea-predominant irritable bowel syndrome: a pilot study. Mayo Clinic Proc. 1992; 67:732–8.
18. Maxton D G, Morris J, Whorwell P J. Selective 5-hydroxytryptamine antagonism: a role in irritable bowel syndrome and functional dyspepsia? Aliment. Pharm. Ther. 1996; 10:595–9.
19. Goldberg P A, Kamm M A, Setti-Carraro P, van der Sijp J R M, Roth C. Modification of visceral sensitivity and pain in irritable bowel syndrome by 5-$HT_3$ antagonism (ondansetron). Digestion 1996; 57:478–83.
20. von der Ohe M R, Hanson R B, Camilleri M. Serotonergic mediation of postprandial colonic tonic and phasic responses in humans. Gut 1994; 35:536–41.
21. Prior A, Read N W. Reduction of rectal sensitivity and post-prandial motility by granisetron, a 5-$HT_3$-receptor antagonist, in patioents with irritable bowel syndrome. Aliment. Pharm. Ther. 1993; 7:175–80.
22. Bardhan K, Bodemar G, Geldof H, Schutz E, Snell C, Darekar B. A double-blind, placebo-controlled study to evaluate the efficacy of alosetron in the treatment of irritable bowel syndrome. Gastroenterology 1996; 110:A630.

23. Forster J M, Houghton L A, Whorwell P J. Alosetron slows colonic transit in patients with irritable bowel syndrome. Gastroenterology 1997; 112:A732.
24. Harding J, Reynolds L, Sorrells S, Haw J, Mangel A, Webb D, Northcutt A. A novel electronic data collection system for symptoms in IBS. Gastroenterology 1997; 112:A745.
25. Harding J P, Hamm L R, Ehsanullah R S B, Heath A T, Sorrells S C, Haw J, Dukes G E, Wolfe S G, Mangel A W, Northcutt A R. Use of a novel electronic data collection system in multicenter studies of irritable bowel syndrome. Aliment. Pharm. Ther. 1997. In Press.
26. Mangel A W, Hahn B A, Heath A T, Northcutt A R, Kong S, Dukes G D, McSorley D. Adequate relief as an endpoint in clinical trials in irritable bowel syndrome. Aliment. Pharm. Ther. 1997; Submitted.

What is claimed is:

1. A method of treatment of pain associated with non-constipated female IBS which comprises administering an effective amount of a 5-$HT_3$ receptor antagonist or a pharmaceutically acceptable derivative thereof.

2. A method of treatment according to claim 1, wherein the 5-$HT_3$ receptor antagonist is alosetron or a pharmaceutically acceptable derivative thereof.

3. A method of treatment according to claim 2, wherein alosetron is in the form of its hydrochloride.

4. A method of treatment according to claim 1, wherein the 5-$HT_3$ receptor antagonist is selected from granisetron, azasetron, tropisetron, ramosetron, ondansetron, lerisetron, (R) zacopride, cilansetron, itasetron, indisetron and dolasetron.

5. A method of improving stool consistency in a patient afflicted with non-constipated female IBS which comprises administering an effective amount of a 5-$HT_3$ receptor antagonist or a pharmaceutically acceptable derivative thereof.

6. A method of treatment according to claim 5, wherein the 5-$HT_3$ receptor antagonist is alosetron or a pharmaceutically acceptable derivative thereof.

7. A method of treatment according to claim 6, wherein alosetron is in the form of its hydrochloride.

8. A method of treatment according to claim 5, wherein the 5-$HT_3$ receptor antagonist is selected from granisetron, azasetron, tropisetron, ramosetron, ondansetron, lerisetron, (R) zacopride, cilansetron, itasetron, indisetron and dolasetron.

9. A method of decreasing urgency in a subject afflicted with non-constipated female IBS which comprises administering an effective amount of a 5-$HT_3$ receptor antagonist or a pharmaceutically acceptable derivative thereof.

10. A method of treatment according to claim 9, wherein the 5-$HT_3$ receptor antagonist is alosetron or a pharmaceutically acceptable derivative thereof.

11. A method of treatment according to claim 10, wherein alosetron is in the form of its hydrochloride.

12. A method of treatment according to claim 9, wherein the 5-$HT_3$ receptor antagonist is selected from granisetron, azasetron, tropisetron, ramosetron, ondansetron, lerisetron, (R) zacopride, cilansetron, itasetron, indisetron and dolasetron.

* * * * *